(12) United States Patent
Zhou et al.

(10) Patent No.: US 12,076,443 B2
(45) Date of Patent: Sep. 3, 2024

(54) PREPARATION METHOD OF NANOZYME COMPOSITE-BASED HYBRID HYDROGEL EYE DROP

(71) Applicant: INSTITUTE OF OPHTHALMOLOGY AFFILIATED TO SHANDONG FIRST MEDICAL UNIVERSITY (SHANDONG INSTITUTE OF OPHTHALMOLOGY, QINGDAO EYE HOSPITAL AFFILIATED TO SHANDONG FIRST MEDICAL UNIVERSITY), Shandong (CN)

(72) Inventors: Qingjun Zhou, Qingdao (CN); Weiyun Shi, Qingdao (CN); Hongwei Wang, Qingdao (CN); Fangying Song, Qingdao (CN)

(73) Assignee: INSTITUTE OF OPHTHALMOLOGY AFFILIATED TO SHANDONG FIRST MEDICAL UNIVERSITY (SHANDONG INSTITUTE OF OPHTHALMOLOGY, QINGDAO EYE HOSPITAL AFFILIATED TO SHANDONG FIRST MEDICAL UNIVERSITY), Qingdao (CN)

( * ) Notice: Subject to any disclaimer, the term of this patent is extended or adjusted under 35 U.S.C. 154(b) by 0 days.

(21) Appl. No.: 18/572,198

(22) PCT Filed: Feb. 15, 2023

(86) PCT No.: PCT/CN2023/076110
§ 371 (c)(1),
(2) Date: Dec. 20, 2023

(87) PCT Pub. No.: WO2024/031949
PCT Pub. Date: Feb. 15, 2024

(65) Prior Publication Data
US 2024/0261231 A1   Aug. 8, 2024

(30) Foreign Application Priority Data
Aug. 11, 2022   (CN) .......................... 202210964063.3

(51) Int. Cl.
*A61K 9/16* (2006.01)
*A61K 9/00* (2006.01)
*A61K 9/06* (2006.01)
*A61K 9/50* (2006.01)
*A61K 9/51* (2006.01)

(52) U.S. Cl.
CPC .......... *A61K 9/5169* (2013.01); *A61K 9/0048* (2013.01); *A61K 9/06* (2013.01); *A61K 9/5123* (2013.01); *A61K 9/5192* (2013.01)

(58) Field of Classification Search
None
See application file for complete search history.

(56) References Cited

U.S. PATENT DOCUMENTS

2010/0251856 A1   10/2010   Santhanam et al.

FOREIGN PATENT DOCUMENTS

| CN | 114129766 A | 3/2022 |
|---|---|---|
| CN | 115300459 A | 11/2022 |
| JP | 2000204182 A | 7/2000 |

OTHER PUBLICATIONS

Zhang Guo-Chao, et al., Preparation of cobalt-silver nanoparticles and preliminary study on its antibacterial activity, Electronic Journal of Translational Medicine, 2017, pp. 39-41, vol. 4 No. 11.

*Primary Examiner* — Michael G. Hartley
*Assistant Examiner* — Melissa J Perreira
(74) *Attorney, Agent, or Firm* — Bayramoglu Law Offices LLC (57) ABSTRACT

A preparation method of a nanozyme composite-based hybrid hydrogel eye drop includes synthesizing a tannin-coordinated silver/cobalt composite nanoparticle through a coordination reaction of cobalt chloride hexahydrate with ammonia water and an oxidation-reduction reaction of silver nitrate with tannin; and mixing the silver/cobalt composite nanoparticle with an acrylate-modified gelatin, conducting an ultrasonic treatment to allow complete dissolution, and irradiating a resulting mixture under ultraviolet (UV) light to obtain the nanozyme composite-based hybrid hydrogel eye drop. The preparation method of the present disclosure has simple operations and a short preparation time. The eye drop prepared by the preparation method shows a broad-spectrum bactericidal effect against a variety of bacteria and fungi, and has prominent preventive and therapeutic effects for bacterial and drug-resistant bacterial corneal infections.

10 Claims, 8 Drawing Sheets

PREPARATION METHOD OF NANOZYME COMPOSITE-BASED HYBRID HYDROGEL EYE DROP

CROSS REFERENCE TO THE RELATED APPLICATIONS

This application is the national phase entry of International Application No. PCT/CN2023/076110, filed on Feb. 15, 2023, which is based upon and claims priority to Chinese Patent Application No. 202210964063.3, filed on Aug. 11, 2022, the entire contents of which are incorporated herein by reference.

TECHNICAL FIELD

The present disclosure belongs to the field of eye drops, and specifically relates to a preparation method of a nanozyme composite-based hybrid hydrogel eye drop.

BACKGROUND

Bacterial keratitis is an infection caused by bacteria invading the cornea that has a rapid onset and can cause corneal ulcers or even corneal perforation in severe cases. Bacterial keratitis is one of the major blinding eye diseases in developing countries. The most common factors for causing bacterial keratitis include: use of contact lenses, especially wearing contact lenses at night or for a long time and inadequate sterilization of lenses; traumas; eye surgery, especially corneal surgery; chronic ocular surface diseases; and systemic diseases such as diabetes and/or long-term use of topical corticosteroids. Among common bacterial pathogens, the most common pathogens causing keratitis include *Staphylococcus aureus* (*S. aureus*), *Pseudomonas aeruginosa* (*P. aeruginosa*), *Streptococcus pneumoniae* (*S. pneumoniae*), and *Serratia*, where keratitis caused by infection with *P. aeruginosa* is the most severe and difficult to treat. Clinically, the treatment of *P. aeruginosa*-induced keratitis is mainly based on the clearance of lesions and the frequent use of topical antibiotics to control the development of corneal ulcers as efficiently and rapidly as possible. However, the use of antibiotics comes with some risks and problems. The retrospective analysis of a clinical trial for treating bacterial keratitis with topical antibiotics shows that the use of aminoglycosides and cephalosporins has a higher relative risk of causing minor adverse events such as ocular discomfort or chemical conjunctivitis than the use of fluoroquinolones. The retrospective analysis of drug resistance of *P. aeruginosa* isolated from the ocular surface shows that, although average resistance rates of *P. aeruginosa* to common ocular antibiotics such as ciprofloxacin (9%), gentamicin (22%), and ceftazidime (13%) are relatively low, the resistance rates of *P. aeruginosa* to common ocular antibiotics tend to increase year by year. Therefore, it is still urgent and necessary to develop a novel antibacterial drug for treating *P. aeruginosa*-induced keratitis.

SUMMARY

In view of the problem that the drug resistance of pathogens causing keratitis to common ocular antibiotics tends to increase and thus novel antibacterial drugs are urgently needed, the present disclosure provides a preparation method of a nanozyme composite-based hybrid hydrogel eye drop, including: synthesizing a tannin-coordinated silver/cobalt composite nanoparticle (TCN) through a coordination reaction of cobalt chloride hexahydrate with ammonia water and an oxidation-reduction reaction of silver nitrate with tannin; mixing the tannin-coordinated silver/cobalt composite nanoparticle and an acrylate-modified gelatin with water as a medium, conducting an ultrasonic treatment to obtain a homogeneous mixture, and irradiating the homogeneous mixture under ultraviolet (UV) light to obtain a nanozyme composite-based hybrid hydrogel material (TCNH); and thoroughly mixing the nanozyme composite-based hybrid hydrogel material with a hydrogen peroxide solution to obtain the nanozyme composite-based hybrid hydrogel eye drop. The eye drop prepared by the preparation method shows a broad-spectrum bactericidal effect against a variety of bacteria and fungi, and has prominent preventive and therapeutic effects for bacterial and drug-resistant bacterial corneal infections.

The preparation method of a nanozyme composite-based hybrid hydrogel eye drop provided by the present disclosure includes the following steps:

(1) adding a small amount of ammonia water dropwise to a cobalt chloride aqueous solution, and allowing a reaction for a specified time; and further adding a cobalt chloride aqueous solution dropwise, and allowing a reaction;

(2) completely dissolving silver acetate in ammonia water to obtain a Tollens' reagent, slowly adding the Tollens' reagent dropwise to a reaction solution obtained in step (1), and stirring for a period of time; adding a tannin solution dropwise to obtain a fourth system, and further stirring the fourth system to allow precipitation; and centrifuging a resulting mixture, washing and drying a resulting precipitate, and calcining the dried precipitate at 350° ° C. to 450° ° C. for 1 h to 4 h to obtain a tannin-coordinated silver/cobalt composite nanoparticle; and (3) adding the tannin-coordinated silver/cobalt composite nanoparticle to a 5 wt % to 7.5 wt % acrylate-modified gelatin aqueous solution, adding a solution of benzoin dimethyl ether in ethanol as an initiator, and conducting an ultrasonic treatment to obtain a homogeneous mixture; irradiating the homogeneous mixture under UV light to produce a gelatinous aqueous solution; and adding a hydrogen peroxide solution, and conducting an ultrasonic treatment at room temperature to uniformity to obtain the nanozyme composite-based hybrid hydrogel eye drop.

Further, a concentration of the cobalt chloride aqueous solution is 20 mmol/L to 30 mmol/L.

Further, the ammonia water is an aqueous solution with 20% to 28% of ammonia.

Further, the step (1) includes: adding the ammonia water dropwise to the cobalt chloride aqueous solution, gradually heating to 55° C. to 65° C., and stirring for 12 min to 18 min; and further adding the cobalt chloride aqueous solution dropwise, and allowing the reaction for 1 h to 4 h.

Further, in the step (2), the Tollens' reagent is slowly added dropwise, and the stirring is conducted for 15 min; and the tannin solution is slowly added dropwise, and the stirring is conducted for 16 h at room temperature.

Further, in the step (2), the resulting precipitate is washed with water and ethanol successively, then dried at 60° C. for 4 h, and then calcined at 400° C. for 3 h.

Further, the acrylate-modified gelatin is methylacrylate-modified gelatin.

Further, in the homogeneous mixture in the step (3), a mass concentration of the acrylate-modified gelatin is 2.0% to 6.0%.

Further, in the step (3), the homogeneous mixture is irradiated under the UV light for 12 min to 18 min.

Further, in the homogeneous mixture in the step (3), a mass ratio of the acrylate-modified gelatin to the tannin-coordinated silver/cobalt composite nanoparticle is (8-12):1.

Beneficial effects of the present disclosure: The preparation method of the present disclosure has simple operations and a short preparation time. The eye drop prepared by the preparation method shows a broad-spectrum bactericidal effect against a variety of bacteria and fungi, and has prominent preventive and therapeutic effects for bacterial and drug-resistant bacterial corneal infections.

DETAILED DESCRIPTION OF THE EMBODIMENTS

The present disclosure is further described in detail below with reference to a specific embodiment.

Example (1) 238.0 mg of cobalt chloride hexahydrate was added to a centrifuge tube.
(2) 50.0 mL of water was added to the centrifuge tube in the step (1), and a resulting mixture was ultrasonically treated to allow complete dissolution.
(3) 1.0 mL of 25% ammonia water was added dropwise to the centrifuge tube in the step (2), and a resulting mixed solution was gradually heated to 60° C. and stirred for 15 min.
(4) 20.0 mL of a 25 mmol/L cobalt chloride hexahydrate solution was added to the centrifuge tube in the step (3), and a reaction was conducted for 3 h.
(5) 250.3 mg of silver acetate was added to 10 mL of 25% ammonia water, and a resulting mixture was ultrasonically treated to allow complete dissolution.
(6) A Tollens' reagent obtained in the step (5) was slowly added dropwise to a reaction solution obtained in the step (4), and a resulting system was stirred for 15 min.
(7) 2.34 g of tannin was added to 40.0 mL of water, and a resulting mixture was ultrasonically treated to allow complete dissolution.
(8) A tannin solution obtained in the step (7) was slowly added dropwise to a reaction solution obtained in the step (6), and a resulting system was stirred at room temperature for 16 h.
(9) A mixture obtained in the step (8) was centrifuged, and a resulting precipitate was washed with water and ethanol, dried at 60° C. for 4 h, and then calcined at 400° C. for 3 h to obtain TCN.
(10) 150 mg of a 7.5 wt % acrylate-modified gelatin was added to a centrifuge tube.
(11) 3.0 mL of water was added to the centrifuge tube in the step (10), and a resulting mixture was ultrasonically treated to allow complete dissolution.
(12) 15.0 mg of the TCN and 2 μL of a solution of 10 wt % benzoin dimethyl ether in ethanol were added to the centrifuge tube, and an ultrasonic treatment was conducted to obtain a homogeneous mixture.
(13) The centrifuge tube in the step (12) was irradiated under UV light for 15 min, where due to a relatively-low concentration of the acrylate-modified gelatin, slight cross-linking occurred with benzoin dimethyl ether as a photoinitiator to produce a gelatinous aqueous solution in which TCNs were evenly dispersed.
(14) A hydrogen peroxide solution was added to the centrifuge tube in step (13), and an ultrasonic treatment was conducted at room temperature to obtain a homogeneous TCNH eye drop.

Antibacterial Experiment

The TCNH eye drop prepared in the above embodiment was used in in vitro antibacterial experiments for *Escherichia coli* (*E. coli*), *P. aeruginosa*, drug-resistant *P. aeruginosa*, and *Candida albicans* (*C. albicans*) and in vivo prevention and treatment experiments for corneal infections caused by *P. aeruginosa* and drug-resistant *P. aeruginosa*.

Figure 1:
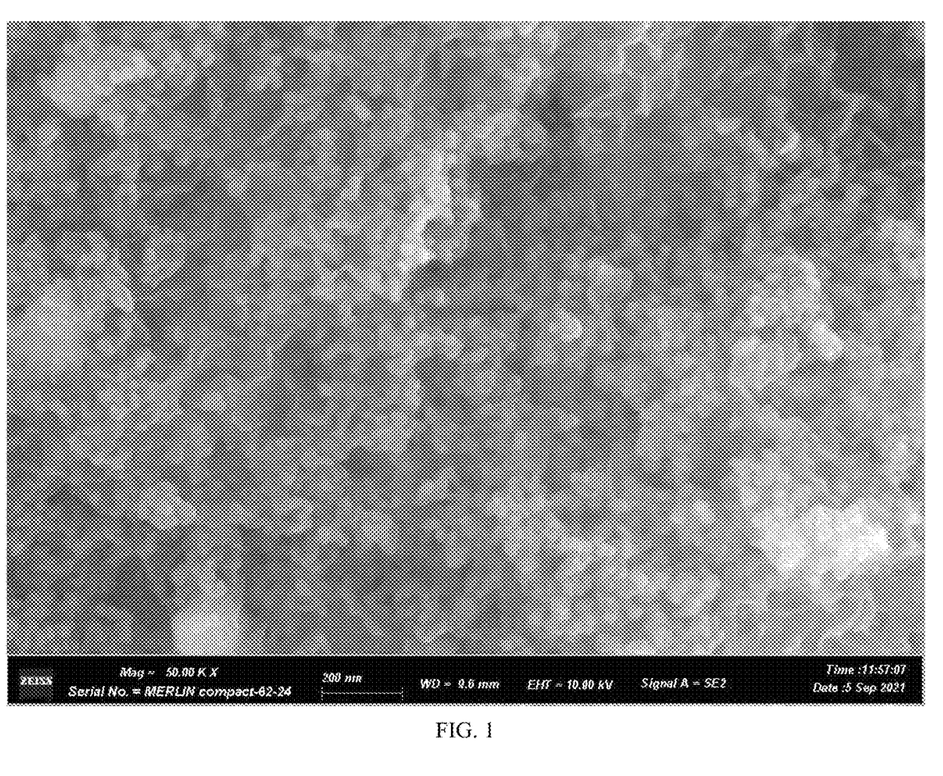
FIG. 1 is a scanning electron microscopy (SEM) image of a TCN nanozyme prepared in an embodiment, where it can be seen that the nanozyme has a spherical accumulation morphology.
Figure 2:
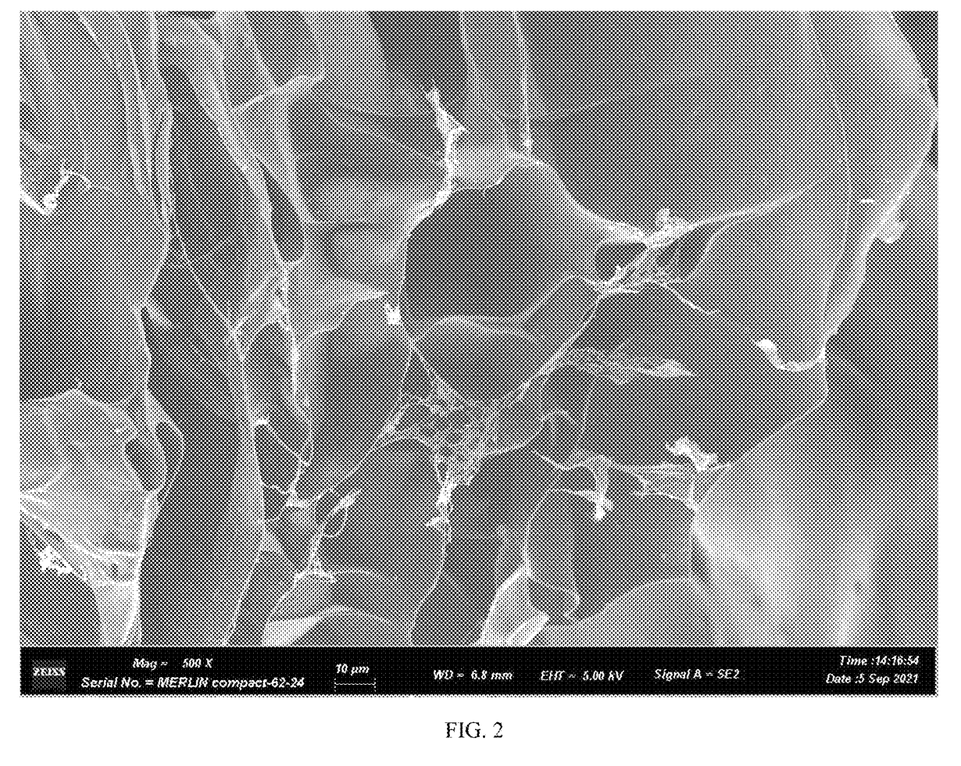
FIG. 2 is an SEM image of a TCNH eye drop prepared in an embodiment, where it can be seen that the eye drop has a typical hydrogel morphology with macropores of tens of microns.
Figure 3:
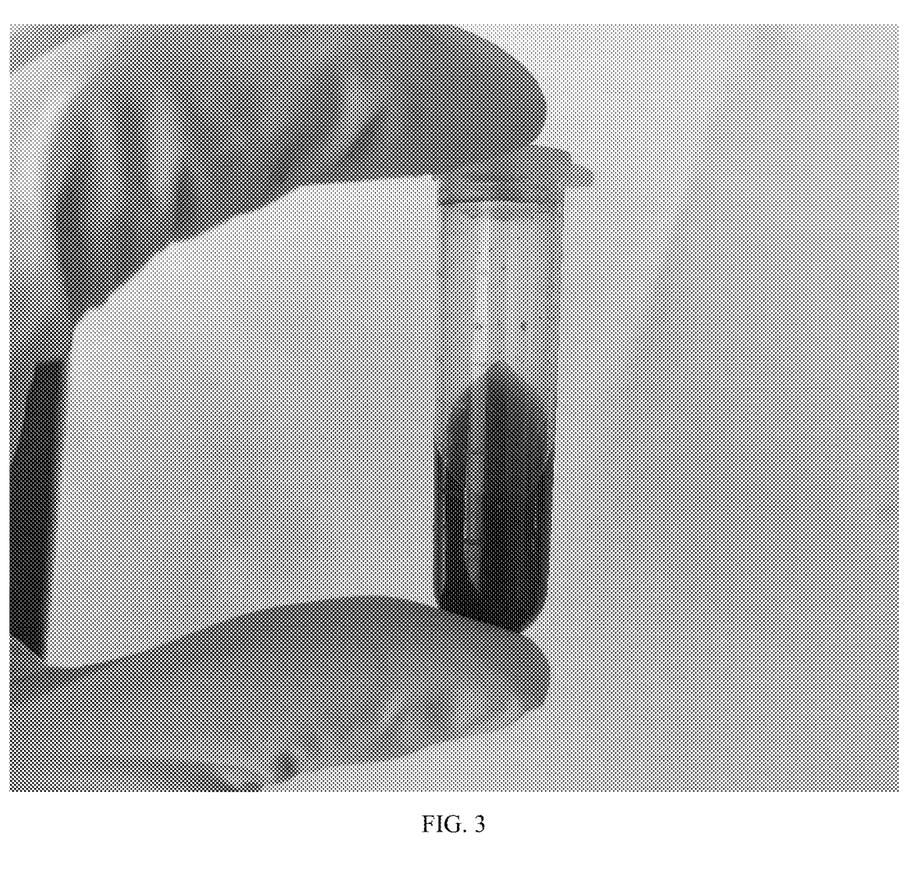
FIG. 3 is an optical photograph of a TCNH eye drop prepared in an embodiment, where it can be seen that a nanozyme is evenly dispersed in the eye drop.
Figure 4:
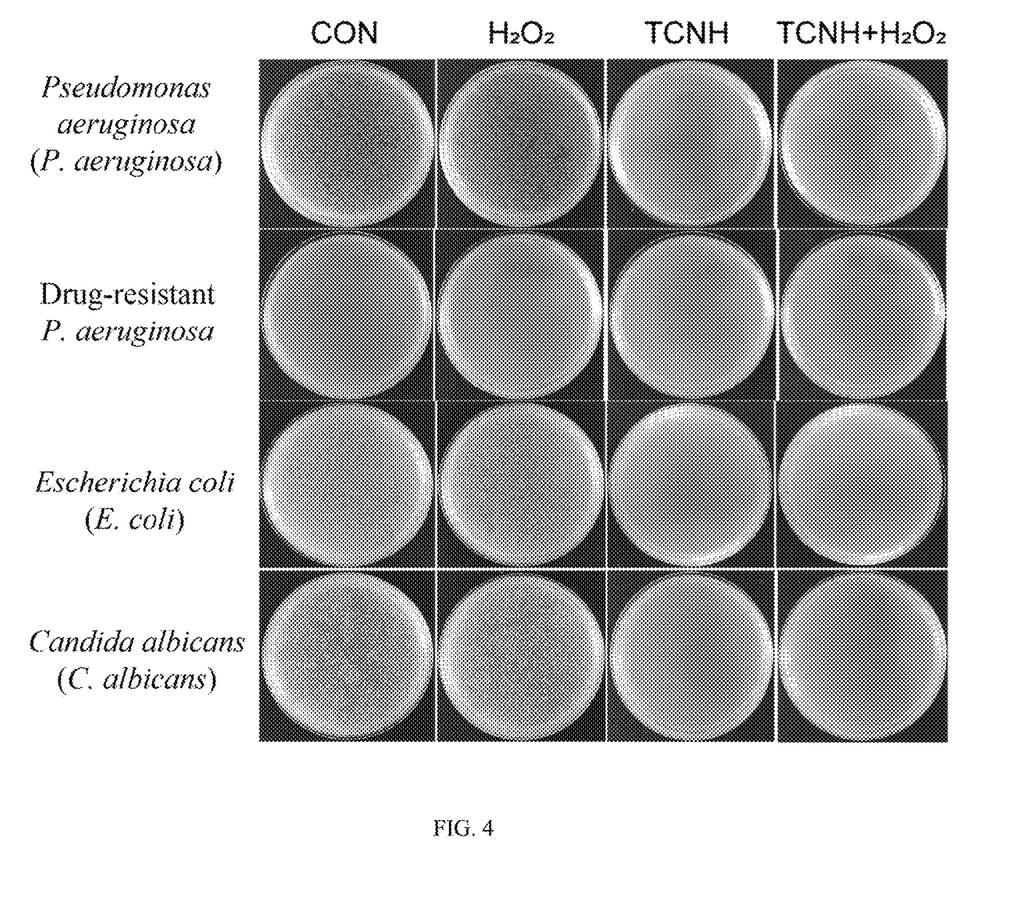
FIG. 4 shows results of an in vitro antibacterial experiment (a plate experiment) of a TCNH eye drop prepared in an embodiment.
Figure 5:
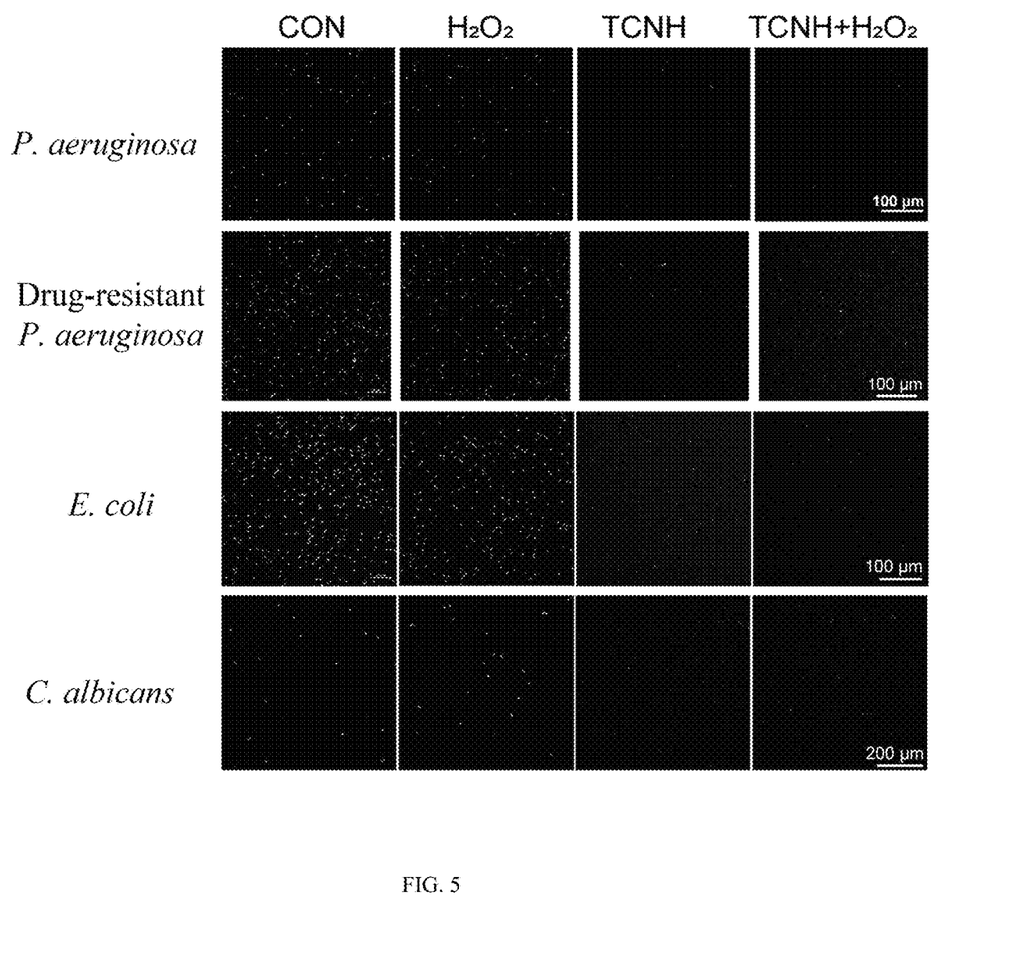
FIG. 5 shows numbers of viable bacteria stained green in a control group and a $H_2O_2$ group during an in vitro antibacterial experiment of a TCNH eye drop prepared in an embodiment.
Figure 6:
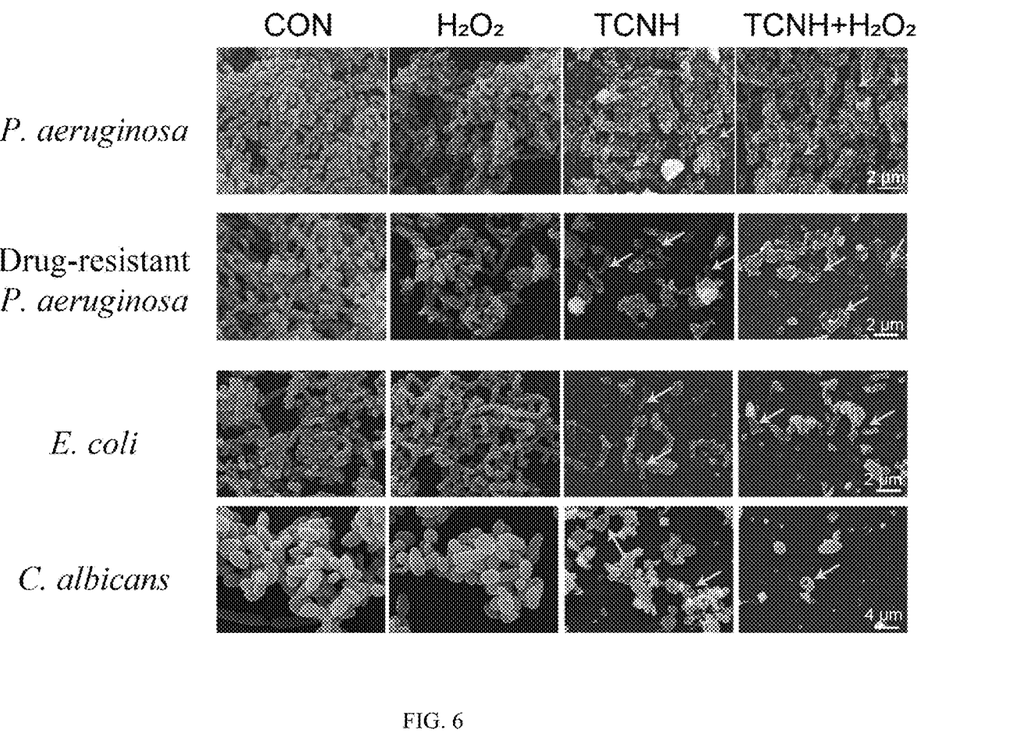
FIG. 6 shows SEM images of bacteria in a control group and a $H_2O_2$ group during an in vitro antibacterial experiment of a TCNH eye drop prepared in an embodiment.

FIG. 4 to FIG. 6 show results of the in vitro antibacterial experiments of the TCNH eye drop. Antibacterial effects of *P. aeruginosa*, drug-resistant *P. aeruginosa*, *E. coli*, and *C. albicans*: As shown in FIG. 4, plates in a control group and a $H_2O_2$ group are overgrown with bacteria, and plates in a TCNH group and a TCNH+$H_2O_2$ group are free of bacterial colonies. As shown in FIG. 5, in a control group and a $H_2O_2$ group, there are a large number of live bacteria stained green and a small number of dead bacteria stained red; and in a TCNH group and a TCNH+$H_2O_2$ group, a number of bacteria is significantly reduced, and there are only a few of scattered bacteria in a field of vision. As shown in FIG. 6, bacteria in a control group and a $H_2O_2$ group have a regular and intact morphology under a scanning electron microscope, and bacteria in a TCNH group and a TCNH+$H_2O_2$ group have an irregular morphology with obvious shrinkage or even depression.

Figure 7A:
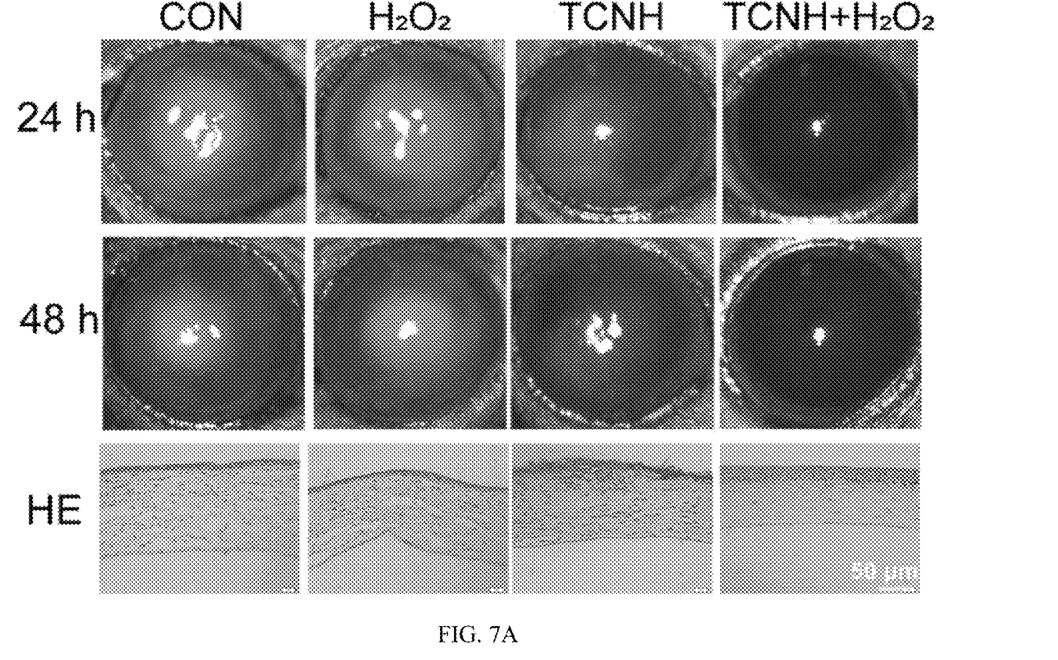
FIGS. 7A-7B show obvious corneal infections in a control group and a $H_2O_2$ group during an in vivo antibacterial experiment (*P. aeruginosa*) of a TCNH eye drop prepared in an embodiment.
Figure 7B:
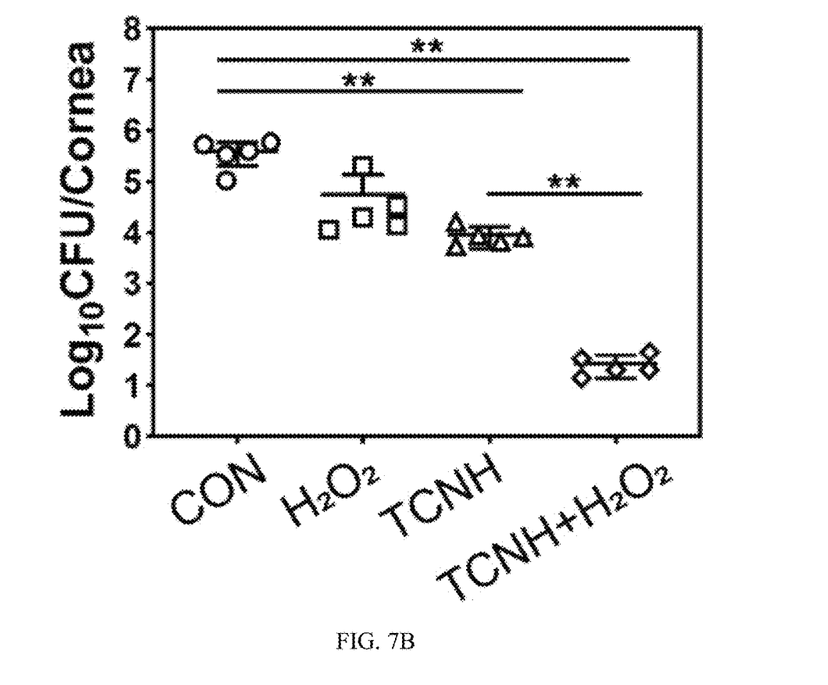

Results of the in vivo antibacterial experiments of the TCNH eye drop (*P. aeruginosa*) are shown in FIGS. 7A-7B, and it can be seen that a cornea is obviously infected in a control group and a $H_2O_2$ group, a cornea is slightly infected in a TCNH group, and a cornea is not infected in a TCNH+$H_2O_2$ group. Statistics of numbers of bacteria in corneas show that a number of bacteria in a TCNH group is significantly reduced by an order of magnitude.

Figure 8A:
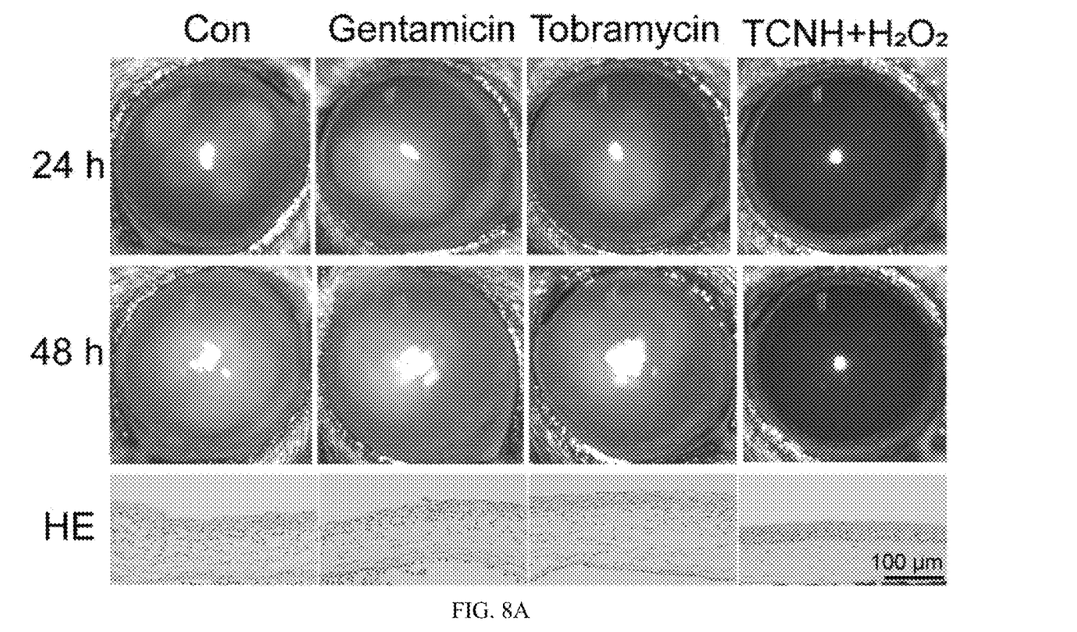
FIGS. 8A-8B show results of an in vivo antibacterial experiment (a drug-resistant *P. aeruginosa* strain) of a TCNH eye drop prepared in an embodiment.
Figure 8B:
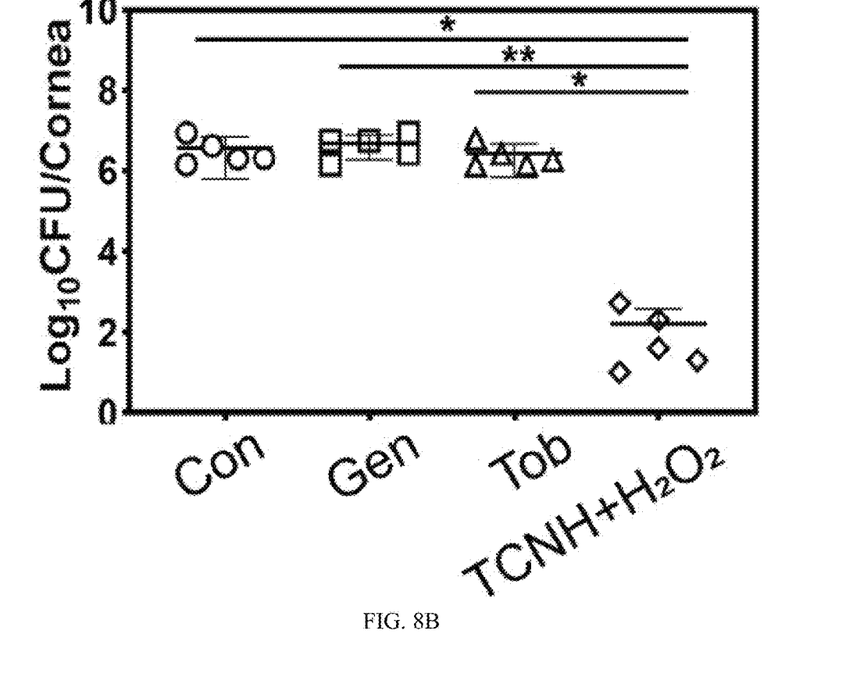

Results of an in vivo antibacterial experiment (a drug-resistant *P. aeruginosa* strain) of the TCNH eye drop are shown in FIGS. 8A-8B, and it can be seen that there is a significant infection in a control group, a gentamicin group (Gen), and a tobramycin group (Tob) and there is no infection in a TCNH+H$_2$O$_2$ group. Statistics of numbers of bacteria in corneas show that a number of drug-resistant bacteria in a TCNH group is significantly reduced by an order of magnitude.

The above embodiments are only intended to describe the preferred implementations of the present disclosure, but not to limit the scope of the present disclosure. Various alterations and improvements made by those of ordinary skill in the art to the technical solution of the present disclosure without departing from the design spirit of the present disclosure shall fall within the protection scope of the appended claims of the present disclosure.

What is claimed is:

1. A preparation method of a nanozyme composite-based hybrid hydrogel eye drop, comprising the following steps:
    (1) adding a small amount of ammonia water dropwise to a cobalt chloride aqueous solution, gradually heating to 55° C. to 65° C., and stirring for 12 min to 18 min; and further adding a cobalt chloride aqueous solution dropwise, and allowing a reaction for 1 h to 4 h;
    (2) completely dissolving silver acetate in ammonia water to obtain a Tollens' reagent, slowly adding the Tollens' reagent dropwise to a reaction solution obtained in step (1), and stirring for a period of time; adding a tannin solution dropwise, and further stirring to allow precipitation; and centrifuging, washing and drying a resulting precipitate, and calcining at 350° C. to 450° C. for 1 h to 4 h to obtain a tannin-coordinated silver/cobalt composite nanoparticle; and
    (3) adding the tannin-coordinated silver/cobalt composite nanoparticle to a 5 wt % to 7.5 wt % acrylate-modified gelatin aqueous solution, adding a solution of benzoin dimethyl ether in ethanol as an initiator, and conducting an ultrasonic treatment to obtain a homogeneous mixture; irradiating the homogeneous mixture under ultraviolet (UV) light to produce a gelatinous aqueous solution; and adding a hydrogen peroxide solution, and conducting an ultrasonic treatment at room temperature to uniformity to obtain the nanozyme composite-based hybrid hydrogel eye drop.

2. The preparation method according to claim 1, wherein a concentration of the cobalt chloride aqueous solution is 20 mmol/L to 30 mmol/L.

3. The preparation method according to claim 1, wherein the ammonia water is an aqueous solution with 20% to 28% of ammonia.

4. The preparation method according to claim 1, wherein in the step (2), the Tollens' reagent is slowly added dropwise, and the stirring is conducted for 15 min; and the tannin solution is slowly added dropwise, and the stirring is conducted for 16 h at room temperature.

5. The preparation method according to claim 1, wherein in the step (2), the resulting precipitate is washed with water and ethanol successively, then dried at 60° C. for 4 h, and then calcined at 400° C. for 3 h.

6. The preparation method according to claim 1, wherein the acrylate-modified gelatin is methylacrylate-modified gelatin.

7. The preparation method according to claim 1, wherein in the homogeneous mixture in the step (3), a mass concentration of the acrylate-modified gelatin is 2.0% to 6.0%.

8. The preparation method according to claim 1, wherein in the step (3), the homogeneous mixture is irradiated under the UV light for 12 min to 18 min.

9. The preparation method according to claim 1, wherein in the homogeneous mixture in the step (3), a mass ratio of the acrylate-modified gelatin to the tannin-coordinated silver/cobalt composite nanoparticle is 8-12:1.

10. The preparation method according to claim 2, wherein in the homogeneous mixture in the step (3), a mass ratio of the acrylate-modified gelatin to the tannin-coordinated silver/cobalt composite nanoparticle is 8-12:1.

* * * * *